US005500211A

United States Patent [19]
George et al.

[11] Patent Number: 5,500,211
[45] Date of Patent: Mar. 19, 1996

[54] SOAP-FREE SELF-FOAMING SHAVE GEL COMPOSITION

[75] Inventors: Robert C. George, Newton, Mass.; Andrew M. Lasota, London, England

[73] Assignee: The Gillette Company, Boston, Mass.

[21] Appl. No.: 310,597

[22] Filed: Sep. 22, 1994

[51] Int. Cl.$^6$ .................................................. A61K 7/15
[52] U.S. Cl. ........................ 424/73; 424/70.31; 424/47; 514/944
[58] Field of Search ................................ 424/73, 70.31, 424/47

[56] References Cited

U.S. PATENT DOCUMENTS

| | | | |
|---|---|---|---|
| 2,995,521 | 8/1961 | Bluard | 252/90 |
| 3,541,581 | 11/1970 | Monson | 252/90 |
| 3,959,160 | 5/1976 | Horsler et al. | 252/90 |
| 4,046,874 | 9/1977 | Gabby et al. | 424/73 |
| 4,113,643 | 9/1978 | Thompson et al. | 252/90 |
| 4,140,648 | 2/1979 | Thompson et al. | 252/90 |
| 4,405,489 | 9/1983 | Sisbarro | 252/315.4 |
| 4,528,111 | 7/1985 | Su | 252/107 |
| 4,651,503 | 3/1987 | Anderson et al. | 53/440 |
| 4,761,279 | 8/1988 | Khalil et al. | 424/73 |
| 4,892,729 | 1/1990 | Cavazza | 424/73 |
| 4,999,183 | 3/1991 | Mackles et al. | 424/47 |
| 5,248,495 | 9/1993 | Patterson et al. | 424/73 |
| 5,308,643 | 5/1994 | Osipow et al. | 424/73 |
| 5,326,556 | 7/1994 | Barnet et al. | 424/73 |
| 5,340,571 | 8/1994 | Grace | 424/73 |

FOREIGN PATENT DOCUMENTS

91/07943  6/1991  WIPO ............................. A61K 7/15

OTHER PUBLICATIONS

Cosmetic and Pharmaceutical Formulary Supplement, Croda, pp. 1–8.
Harry's Cosmeticology, 7th Ed. (1982).
Crodata, Crodasinic LS–30, pp. 1–8, 1994, Jun.

*Primary Examiner*—Thurman K. Page
*Assistant Examiner*—James M. Spear
*Attorney, Agent, or Firm*—Stephan P. Williams

[57] ABSTRACT

The present invention comprises a soap-free self-foaming shave gel composition which maintains superior performance attributes while avoiding the harshness and drying associated with soap-based shave preparations. The shave gel composition of the present invention comprises water, a water-soluble sarcosinate salt, a volatile self-foaming agent, and a non-volatile paraffinic hydrocarbon fluid.

19 Claims, No Drawings

SOAP-FREE SELF-FOAMING SHAVE GEL COMPOSITION

FIELD OF THE INVENTION

This invention relates to a non-soap shave gel composition. Such a composition is dispensed in the form of a gel containing a volatile component that causes the gel to turn into a foam when spread on the skin in preparation for wet shaving—that is, shaving with a razor blade.

BACKGROUND OF THE INVENTION

Post-foaming or self-foaming shave gels are now well-known and have been described, for example, in U.S. Pat. Nos. 2,995,521 (Bluard), 3,541,581 (Monson), 4,405,489 (Sisbarro), 4,528, 111 (Su), 4,651,503 (Anderson), 5,248, 495 (Patterson), 5,308,643 (Osipow), and 5,326,556 (Barnet) and published PCT application WO 91/07943 (Chaudhuri). Such compositions generally take the form of an oil-in-water emulsion in which the self-foaming agent, generally a volatile (i.e. low boiling point) aliphatic hydrocarbon, is solubilized in the oil phase, and the water phase comprises a water-soluble soap component. The product is generally packaged in an aerosol container with a barrier, such as a piston or collapsible bag, to separate the self-foaming gel from the propellant required for expulsion of the product. The product is dispensed as a clear, translucent or opaque gel that is substantially free from foaming until it is spread over the skin, at which time it produces a foam lather generated by the volatilization of the volatile hydrocarbon foaming agent.

While the conventional self-foaming shave gels have gained wide acceptance by consumers, they can be somewhat harsh and drying to the skin due to the soap component. To counteract this effect, the typical shave gel composition is formulated with skin soothing components such as humectants, emollients, silicones, etc. While the addition of such components substantially improve the aesthetics of the product, repeated use can still produce undesirable drying of the skin, particularly among female users. Accordingly, it is highly desirable to develop a self-foaming shave gel composition that is less harsh and drying to the skin than conventional shave gels, without sacrificing any of the performance characteristics thereof.

N-acyl sarcosinates are well-known anionic surfactants represented by the formula

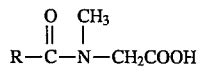

where R is a fatty acid hydrocarbon chain. These materials are typically used in the form of water-soluble salts formed by neutralization with sodium, potassium or ammonium hydroxide or triethanolamine and have been suggested for use in a wide variety of products including shampoos, detergents, dentifrices, hand soaps, and shave creams. For example, aerosol shaving creams containing sarcosinates are disclosed in U.S. Pat. Nos. 3,959,160 (Horsler), 4, 113,643 (Thompson), and 4,140,648 (Thompson) and in Harry's Cosmeticology (7th ed., 1982), p. 169 (see Croda Cosmetic and Pharmaceutical Formulary Supplement, formula SV11 ). A soap-free non-aerosol shave cream which may optionally contain a sarcosinate is disclosed in U.S. Pat. No. 4,892,729 (Cavazza) and a non-aerosol shave gel which contains both a soap and a sarcosinate is disclosed in U.S. Pat. No. 5,340,571 (Grace).

Soap-free shaving products are also known, but have met with limited acceptance. For example, U.S. Pat. Nos. 4,046, 874 (Gabby) and 4,761,279 (Khalil) disclose shaving cream compositions containing respectively a polyglycerol fatty ester (e.g. triglycerol monostearate) and a fatty ester of lactylic acid (e.g. sodium salt of stearyl lactylic acid). A pre-shave gel containing polyethylene oxide polymer and polysulfonic acid polymer is disclosed in U.S. Pat. No. 4,999,183 (Mackles).

SUMMARY OF THE INVENTION

The present invention comprises a soap-free self-foaming shave gel composition which maintains superior performance attributes while avoiding the harshness and drying associated with soap-based shave preparations. The shave gel composition of the present invention comprises water, a water-soluble N-acyl sarcosinate salt, a volatile self-foaming agent, and a non-volatile paraffinic hydrocarbon fluid.

DETAILED DESCRIPTION OF THE INVENTION

The essential components of the shaving composition of the present invention include, in percent by weight, about 65 to 85% water, about 4 to 16% N-acyl sarcosine wherein the acyl group has 10 to 20 carbon atoms, sufficient base to solubilize the N-acyl sarcosine and provide a pH of about 4 to about 8, about 1 to 8% self-foaming agent, and about 1 to 10% non-volatile paraffinic hydrocarbon fluid, said composition being in the form of a self-foaming gel and being substantially free of soap. Preferably the composition will comprise about 70 to 80% water, about 6 to 12% N-acyl sarcosine, sufficient base to provide a pH of about 5 to 7, about 2 to 5% self-foaming agent, and about 1.5 to 7% non-volatile paraffinic hydrocarbon fluid. A more preferred shaving composition will also additionally include a non-ionic surfactant, a fatty alcohol and a gelling aid, and will be subtantially free of other anionic surfactants.

The N-acyl sarcosine may be selected from any of those which are commercially available that have an acyl moiety with 10 to 20, preferably 12 to 18, carbon atoms and that will provide a water-soluble sarcosinate when neutralized with an appropriate base. These typically include stearoyl sarcosine, myristoyl sarcosine, oleoyl sarcosine, lauroyl sarcosine, cocoyl sarcosine and mixtures thereof. Stearoyl sarcosine and myristoyl sarcosine, as well as mixtures thereof, are preferred. It is also possible to utilize a pre-neutralized sarcosinate, such as triethanolamine myristoyl sarcosinate, in which case it will not be necessary to separately add base to the composition except for such amount of acid or base as required to adjust the pH of the final composition. Both the sarcosine component and the base component should be selected so as to provide a clear or translucent gel when combined with the other components of the composition.

The base may be selected from any of the organic amine bases which are typically utilized to neutralize N-acyl sarcosines to form water-soluble salts. These include, for example, isopropanolamine, mono-, di- and triethanolamine, aminomethyl propanol and aminomethyl propanediol. Triethanolamine is preferred. The amount of base which is utilized will depend on the amount of sarcosine which is present in the composition. A sufficient amount should be utilized to solubilize the sarcosine in the aqueous phase of the composition and provide a pH of about 4 to 8, preferably about 5 to 7. To arrive at this pH range the sarcosine must be about 50 to 90% neutralized, preferably about 60 to 80% neutralized. It is, thus, most preferred that there is at least a slight molar excess of sarcosine to base. Typically, the base will comprise about 1 to 6% of the composition.

The self-foaming agent may be any volatile hydrocarbon or halogenated hydrocarbon with a sufficiently low boiling point that it will volatilize and foam the gel upon application to the skin, but not so low that it causes the gel to foam prematurely. The typical boiling point of such an agent generally falls within the range of 20° to 40° C. Preferred self-foaming agents are selected from saturated aliphatic hydrocarbons having 4 to 6 carbon atoms, such as n-pentane, isopentane, neopentane, n-butane, isobutane, and mixtures thereof. Most preferred is a mixture of isopentane and isobutane in a weight ratio of about 1:1 to about 3:1. The self-foaming agent will normally be present in an amount comprising about 1 to 8% of the composition, preferably about 2 to 5%.

The shaving composition additionally contains about 1 to 10%, preferably about 1.5 to 7%, of a non-volatile paraffinic hydrocarbon fluid which aids in gelling the composition. The terms "non-volatile" and "fluid" mean that these materials are liquid at room temperature and have a boiling point above 200° C. Such hydrocarbon fluids include mineral oils and branched-chain aliphatic liquids. These fluids typically have from about 16 to about 48, preferably about 20 to about 40, carbon atoms and a viscosity of about 5 to about 100 cs., preferably about 10 to about 50 cs., at 40° C. The preferred non-volatile paraffinic hydrocarbon fluid is selected from mineral oil with a viscosity of about 10 to about 50 cs. at 40° C., hydrogenated polyisobutene with a molecular weight of about 320 to about 420, and mixtures thereof.

Water is the major component of the composition and is used in sufficient quantities to solubilize the surfactant component and form the continuous phase of the emulsion, while providing a stable gel of suitable viscosity with desirable lathering and rinsing properties. It is added in a sufficient amount (q.s.) to bring the total of all components to 100%. The quantity of water in the composition typically falls within the range of about 65 to 85%, preferably about 70 to 80%.

In addition to the above-described essential components, the shaving composition of the present invention may include a variety of other well-known cosmetic ingredients to improve the aesthetics and performance characteristics of the composition.

It is generally desirable to include up to 8%, preferably about 1 to 6%, of a non-ionic surfactant in the composition to improve foam quality, wettability, gel consistency, and rinsability. Suitable non-ionic surfactants will typically have an HLB of 15 or more and must be compatible with the aqueous sarcosinate component. Preferred non-ionic surfactants include the polyoxyethylene ethers of fatty alcohols, acids and amides, particularly those having 10 to 20, preferably 12 to 18, carbon atoms in the fatty moiety and about 8 to 60, preferably 10 to 30, ethylene oxide units. These include, for example, Oleth-20, Steareth-21, Ceteth-20, and Laureth-23. Other non-ionic surfactants include the polyoxyethylene ethers of alkyl substituted phenols, such as Nonoxynol-20, polyethoxylated sorbitan esters of fatty acids, such as Polysorbate-20, lauryl polyglucoside, sucrose laurate, and polyglycerol 8-oleate.

It may also be desirable to include a water-soluble gelling aid or thickening agent in the shaving composition to improve the consistency and stability of the gel, as well as to adjust its viscosity. These may include, for example, hydroxyalkyl cellulose polymers such as hydroxyethyl cellulose and hydroxypropyl cellulose (sold under the trademarks "Natrosol" and "Klucel" respectively), copolymers of acrylic acid and polyallyl sucrose (sold under the trademark "Carbopol"), carboxymethyl cellulose, and cellulose methyl ether (sold under the trademark "Methocel"). Natural or synthetic gums, resins, and starches may also be used. The preferred thickening agents are hydroxyethyl cellulose, hydroxypropyl cellulose, and mixtures thereof. The gelling aid or thickening agent is typically included in an amount of about 0.01 to 5%, preferably about 0.1 to 2%, by weight of the composition.

The shaving composition will also preferably include up to 8%, preferably about 2 to 6%, by weight of a fatty alcohol such as myristyl, lauryl and stearyl alcohol and octyl dodecanol. The term "fatty" is intended to include 10 to 20, preferably 12 to 18, carbon atoms.

It is particularly desirable to include in the composition a cationic conditioning polymer which is substantive to the skin in order to improve lubricity and post-shave skin feel. Such polymers may include polymeric quaternary ammonium salts of hydroxyethyl cellulose such as polyquaternium-10 and polyquaternium-24. These polymers are typically included in an amount of about 0.05 to 2%, preferably about 0.1 to 1%, by weight.

Other useful additives which may be utilized in the composition include humectants such as glycerin, sorbitol, and propylene glycol, emollients including fatty esters such as isopropyl myristate, decyl oleate, 2-ethylhexyl palmitate, PEG-7 glyceryl cocoate, and glyceryl linoleate, propoxylated fatty ethers such as PPG-10 cetyl ether and PPG-11 stearyl ether, di- and triglycerides such as lecithin and caprylic/capric triglyceride, vegetable oils, and similar materials, skin freshening and soothing agents such as menthol, aloe, allantoin, lanolin, collagen and hyaluronic acid, lubricants such as polyethylene oxide, fluorosurfactants, and silicones (e.g. dimethicone, dimethiconol, dimethicone copolyol, stearyl dimethicone, cetyl dimethicone copolyol, phenyl dimethicone, cyclomethicone, etc.), vitamins (including vitamin precursors and derivatives) such as panthenol, tocopherol acetate, and vitamin A palmitate, colorants, fragrances, antioxidants and preservatives.

A preferred shaving composition of the present invention comprises, in percent by weight, about 65 to 85% water, about 4 to 16% N-acyl sarcosine wherein the acyl group has 10 to 20, preferably 12 to 18, carbon atoms, sufficient organic amine base to solubilize the N-acyl sarcosine and provide a pH of about 4 to about 8, about 1 to 8% self-foaming agent, about 1 to 10% non-volatile paraffinic hydrocarbon fluid, about 1 to 8% of a non-ionic surfactant, and about 1 to 8% of a fatty alcohol. Most preferably the composition will comprise about 70 to 80% water, about 6 to 12% N-acyl sarcosine, sufficient base to provide a pH of about 5 to 7, about 2 to 5% self-foaming agent, about 1.5 to 7% non-volatile paraffinic hydrocarbon fluid, about 1 to 6% of a non-ionic surfactant, about 2 to 6% of a fatty alcohol, and about 0.1 to 2% of a thickening agent.

The shaving composition of the present invention may be packaged in any dispenser suitable for dispensing post-foaming shave gels. These include aerosol containers with a barrier, such as a collapsible bag or piston, to separate the gel from the propellant required for expulsion, collapsible tubes, and pump or squeeze containers.

The following examples illustrate representative shave gel compositions of the present invention. All parts and percentages are by weight.

| Component | Ex. 1 | Ex. 2 | Ex. 3 | Ex. 4 | Ex. 5 |
|---|---|---|---|---|---|
| Stearoyl sarcosine | 5.192 | | 3.558 | | 7.500 |
| Myristoyl sarcosine | 1.923 | 8.000 | 3.558 | 7.500 | |
| Triethanolamine (99%) | 2.596 | 2.750 | 2.596 | 2.750 | 2.750 |
| Myristyl alcohol | 2.692 | 4.000 | 2.692 | 4.000 | 3.000 |
| Mineral oil 180/190[1] | 1.923 | | | | |
| Mineral oil 65/75[1] | | 5.000 | 1.442 | 4.500 | 3.000 |
| Hydrog. Polyisobutene[2] | | | 1.442 | | |
| Dimethicone/dimethiconol[3] | 0.192 | | 0.288 | | |
| Stearyl Dimethicone[4] | | | | | 0.250 |
| Oleth-20 | 4.327 | 1.000 | 4.327 | 1.000 | 4.500 |
| Isopentane | 2.887 | 1.900 | 1.925 | 2.887 | 2.887 |
| Isobutane | 0.963 | 1.900 | 1.925 | 0.963 | 0.963 |
| Hydroxyethyl cellulose[5] | 0.240 | 0.250 | 0.240 | 0.400 | 0.400 |
| Hydroxypropyl cellulose[6] | 0.019 | | 0.019 | 0.020 | 0.020 |
| Polyquaternium-10[7] | 0.240 | | 0.144 | 0.200 | 0.250 |
| PEG-14M[8] | 0.144 | | 0.144 | 0.250 | 0.200 |
| PEG-115M[9] | | 0.025 | | | |
| Aloe vera gel | 0.962 | | 0.962 | | 1.000 |
| Frag.,color.,preserv. | q.s. | q.s. | q.s. | q.s. | q.s. |
| Water | 74.854 | 74.424 | 73.892 | 74.484 | 72.724 |

[1] Protol 180/190 and Carnation 65/75 from Witco Corp.
[2] Panalane L-14E from Amoco Chemical
[3] DC 2-1420 from Dow Corning
[4] DC 2503 from Dow Corning
[5] Natrosol 250 HHR from Hercules Inc.
[6] Klucel HFF from Aqualon
[7] Polymer LK from Amerchol
[8] Polyox WSR N-3000 (MW about 300,000) from Union Carbide
[9] Polyox Coagulant (MW about 5 million) from Union Carbide Procedure: Dissolve into the water at room temperature with stirring the hydroxyethyl cellulose, polyquaternium-10, and PEG-14M (or 115M). After about 40 minutes of stirring, heat the aqueous solution to about 85° C., add the sarcosine (which has been pre-melted), myristyl alcohol, mineral oil and/or hydrogenated polyisobutene and mix for about 10 minutes. Add the triethanolamine and Oleth-20 and continue mixing at about 85° C. for about 30 minutes. Cool to 70° C., add the preservative and mix for 10 minutes. Cool to 35° C. and add the silicone, fragrance, colorant, aloe gel and hydroxypropyl cellulose, the latter having been first pre-mixed with about 0.5 parts of water at 55° C., then an additional 3.5 pads of water at room temperature. After cooling to room temperature the mixture is blended with the isopentane/isobutane and packaged in a barrier-type aerosol container.

While the invention has been described in detail with particular reference to preferred embodiments thereof, various modifications and substitutions will be apparent to those skilled in the art and should be considered to fall within the spirit and scope of the invention as defined by the following claims.

What is claimed is:

1. A shaving composition in the form of a self-foaming gel comprising, in percent by weight, about 65 to 85% water, about 4 to 16% N-acyl sarcosine wherein the acyl group has 10 to 20 carbon atoms, about 1 to 6% organic amine base sufficient to solubilize the N-acyl sarcosine and provide a pH of about 4 to about 8, about 1 to 8% self-foaming agent, about 1 to 8% of a non-ionic surfactant, and about 1 to 10% non-volatile paraffinic hydrocarbon fluid, said composition being substantially free of soap.

2. The shaving composition of claim 1 wherein the N-acyl sarcosine is selected from the group consisting of stearoyl sarcosine, myristoyl sarcosine, oleoyl sarcosine, lauroyl sarcosine, cocoyl sarcosine and mixtures thereof.

3. The shaving composition of claim 2 wherein the organic amine base is triethanolamine.

4. The shaving composition of claim 3 wherein the non-volatile paraffinic hydrocarbon fluid has about 20 to about 40 carbon atoms and a viscosity of about 10 to about 50 cs. at 40° C.

5. The shaving composition of claim 4 wherein the self-foaming agent is a volatile hydrocarbon having 4 to 6 carbon atoms or a mixture of such hydrocarbons.

6. A shaving composition in the form of a self-foaming gel comprising, in percent by weight, about 65 to 85% water, about 4 to 16% N-acyl sarcosine wherein the acyl group has 12 to 18 carbon atoms, about 1 to 6% organic amine base sufficient to solubilize the N-acyl sarcosine and provide a pH of about 4 to about 8, about 1 to 8% self-foaming agent, about 1 to 10% non-volatile paraffinic hydrocarbon fluid, about 1 to 8% of a non-ionic surfactant, and about 1 to 8% of a fatty alcohol, said composition being substantially free of soap.

7. The shaving composition of claim 5 additionally comprising about 1 to 8% of a fatty alcohol.

8. The shaving composition of claim 7 wherein the non-volatile paraffinic hydrocarbon fluid is selected from the group consisting of mineral oil, hydrogenated polyisobutene, and mixtures thereof.

9. The shaving composition of claim 8 which comprises about 70 to 80% water, about 6 to 12% N-acyl sarcosine, sufficient organic amine base to provide a pH of about 5 to 7, about 2 to 5% self-foaming agent, and about 1.5 to 7% non-volatile paraffinic hydrocarbon fluid, said composition being subtantially free of other anionic surfactants.

10. The shaving composition of claim 9 additionally comprising about 0.05 to 2% of a cationic conditioning polymer.

11. The shaving composition of claim 10 additionally comprising about 0.01 to 5% of a thickening agent.

12. The shaving composition of claim 11 wherein the cationic conditioning polymer is a polymeric quaternary ammonium salt of hydroxyethyl cellulose.

13. The shaving composition of claim 12 wherein the thickening agent is selected from the group consisting of hydroxyethyl cellulose, hydroxypropyl cellulose, and mixtures thereof.

14. The shaving composition of claim 6 which comprises about 70 to 80% water, about 6 to 12% N-acyl sarcosine, sufficient base to provide a pH of about 5 to 7, about 2 to 5% self-foaming agent, about 1.5 to 7% non-volatile paraffinic hydrocarbon fluid, about 1 to 6% of a non-ionic surfactant, and about 2 to 6% of a fatty alcohol, said composition being substantially free of other anionic surfactants.

15. The shaving composition of claim 14 wherein the N-acyl sarcosine is selected from the group consisting of stearoyl sarcosine, myristoyl sarcosine, oleoyl sarcosine, lauroyl sarcosine, cocoyl sarcosine and mixtures thereof, the organic amine base is triethanolamine, the non-volatile paraffinic hydrocarbon fluid has about 20 to about 40 carbon atoms and a viscosity of about 10 to about 50 cs. at 40° C., and the self-foaming agent is a volatile hydrocarbon having 4 to 6 carbon atoms or a mixture of such hydrocarbons.

16. The shaving composition of claim 15 wherein the non-volatile paraffinic hydrocarbon fluid is selected from the group consisting of mineral oil, hydrogenated polyisobutene, and mixtures thereof, and the self-foaming agent is a mixture of isopentane and isobutane in a weight ratio of about 1:1 to about 3:1.

17. The shaving composition of claim 16 additionally comprising about 0.05 to 2% of a cationic conditioning polymer.

18. The shaving composition of claim 17 additionally comprising about 0.1 to 2% of a thickening agent selected from the group consisting of hydroxyethyl cellulose, hydroxypropyl cellulose, and mixtures thereof.

19. The shaving composition of claim 18 wherein the cationic conditioning polymer is a polymeric quaternary ammonium salt of hydroxyethyl cellulose.

* * * * *